(12) United States Patent
Bowman et al.

(10) Patent No.: US 6,309,998 B1
(45) Date of Patent: Oct. 30, 2001

(54) PROCESS FOR THE DIRECT OXIDATION OF OLEFINS TO OLEFIN OXIDES

(75) Inventors: Robert G. Bowman, Midland, MI (US); Joseph L. Womack, Oakland, CA (US); Howard W. Clark, Midland, MI (US); Joseph J. Maj, Midland, MI (US); George E. Hartwell, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/458,559

(22) Filed: Dec. 9, 1999

Related U.S. Application Data

(62) Division of application No. 09/209,700, filed on Dec. 11, 1998, now Pat. No. 6,031,116, which is a continuation of application No. PCT/US97/11414, filed on Jun. 30, 1997, which is a continuation-in-part of application No. 08/679,605, filed on Jul. 11, 1996, now abandoned.
(60) Provisional application No. 60/021,013, filed on Jul. 1, 1996, provisional application No. 60/026,590, filed on Sep. 20, 1996, and provisional application No. 60/026,591, filed on Sep. 20, 1996.

(51) Int. Cl.$^7$ ............................. B01J 21/06; B01J 21/08
(52) U.S. Cl. ..................... 502/242; 502/60; 502/64; 502/71; 502/77; 502/232; 502/240; 502/243
(58) Field of Search ................... 502/60, 64, 71, 502/77, 232, 240, 242, 243

(56) References Cited

U.S. PATENT DOCUMENTS

| | | |
|---|---|---|
| 4,391,756 | 7/1983 | Kuch et al. . |
| 4,410,501 | 10/1983 | Taramasso et al. . |
| 4,701,428 | 10/1987 | Bellussi et al. . |
| 4,828,812 * | 5/1989 | McCullen et al. ............ 423/326 |
| 4,839,327 | 6/1989 | Haruta et al. . |
| 5,008,414 | 4/1991 | Ramachandran et al. . |
| 5,162,283 | 11/1992 | Moini . |
| 5,354,875 | 10/1994 | Nemeth et al. . |
| 5,525,741 | 6/1996 | Sugita et al. .................. 549/536 |
| 5,777,163 * | 7/1998 | Muller et al. .................. 564/301 |
| 5,874,596 * | 2/1999 | Onozawa et al. ............. 549/531 |
| 5,932,750 * | 8/1999 | Hayashi et al. ............... 549/523 |
| 5,958,367 * | 9/1999 | Ying et al. ..................... 423/701 |
| 5,965,754 | 10/1999 | Clark et al. . |
| 6,008,389 * | 12/1999 | Grosch et al. ................. 549/533 |

FOREIGN PATENT DOCUMENTS

| | | |
|---|---|---|
| 196 00 709 A1 | 7/1997 | (DE) . |
| 0 200 260 A2 | 12/1986 | (EP) . |
| 0 638 362 A1 | 2/1995 | (EP) . |
| 0 709 360 A1 | 5/1996 | (EP) . |
| 0 723 810 A1 | 7/1996 | (EP) . |
| 0 850 936 A1 | 7/1998 | (EP) . |
| 1 409 421 | 10/1975 | (GB) . |
| 4-352771 | 12/1992 | (JP) . |
| 7-8797 | 1/1995 | (JP) . |
| 7-53577 | 6/1995 | (JP) . |
| 8-269029 | 10/1996 | (JP) . |
| 10-5590 | 1/1998 | (JP) . |
| 96/02323 A1 | 2/1996 | (WO) . |
| 97/25143 A1 | 7/1997 | (WO) . |
| 97/34692 A1 | 9/1997 | (WO) . |
| 97/47386 | 12/1997 | (WO) . |
| 99/00188 | 1/1999 | (WO) . |

OTHER PUBLICATIONS

"Activation and Regeneration of a Hydro–Oxidation Catalyst", filed in the United States on Dec. 9, 1999, USSN 60/169,862 (Attorney's Docket No. 44361); Applicant: Deborah H. Parker et al.

"Method of Preparing a Catalyst Containing Gold and Titanium", filed in the United States on Apr. 8, 1999, USSN 60/128,390 (Attorney's Docket No. 44251); Applicant: Alex Kuperman et al.

"Process for the Hydro–Oxidation of Olefins to Olefin Oxides", filed in the United States on Apr. 8, 1999, USSN 60/128,394 (Attorney's Docket No. 44406); Applicant: Alex Kuperman et al.

Haruta, Masatake, "Catalysis of Ultra–fine Gold Particles Deposited on Metal Oxides", Workshop on Environmental Catalysis: The Role of 1B Metals, Ikeda, Osaka, Japan (Nov. 2–3, 1995) pp. 109–118.

Hayashi, Toshio et al., "Selective Partial Oxidation of Hydrocarbons over Au/TiO$_2$ Catalysts", Symposium On Heterogeneous Hydrocarbon Oxidation Presented Before the Division of Petroleum Chemistry, Inc., 211$^{th}$ National Meeting, American Chemical Society, New Orleans, LA (Mar. 24–29, 1996) pp. 71–74.

Kalvachev, Yuri A. et al., "Selective Partial Oxidation of Propylene to Propylene Oxide on Au/Ti–MCM Catalysts in the Presence of Hydrogen and Oxygen", 3$^{rd}$ World Congress on Oxidation Catalysis, R. K. Grasselli et al. (Editors), Elsevier Science B.V. (Pub.) (Sep. 24, 1997) pp. 965–972.

Derwent 95–092265/13 (EP 640598–A1), Mar. 1995. Abstract only considered.

* cited by examiner

*Primary Examiner*—Elizabeth D. Wood
(74) *Attorney, Agent, or Firm*—Marie F. Zuckerman

(57) ABSTRACT

A process and catalyst for the direct oxidation of an olefin having three or more carbon atoms, such as propylene, by oxygen to the corresponding olefin oxide, such as propylene oxide. The process involves contacting the olefin with oxygen under reaction conditions in the presence of hydrogen and in the presence of a catalyst. The catalyst comprises gold on a titanosilicate, preferably a microporous or mesoporous titanosilicate, such as, TS-1, TS-2, Ti-beta, Ti-ZSM-48, or Ti-MCM-41. Selectivity to the olefin oxide is high at good conversions of the olefin. The catalyst is readily regenerated, and the time between catalyst regenerations is long.

23 Claims, No Drawings

PROCESS FOR THE DIRECT OXIDATION OF OLEFINS TO OLEFIN OXIDES

CROSS-REFERENCES TO RELATED APPLICATIONS

This application is a divisional of U.S. application Ser. No. 09/209,700, filed Dec. 11, 1998, now U.S. Pat. No. 6,031,116 and such U.S. application Ser. No. 09/209,700 is hereby incorporated herein by reference. U.S. application Ser. No. 09/209,700 was a continuation of International Patent Application No. PCT/US97/11414, filed Jun. 30, 1997, which was a continuation-in-part of U.S. application Ser. No. 08/679,605, filed Jul. 11, 1996, and now abandoned. This application also claims the benefit of U.S. Provisional Application No. 60/021013, filed Jul. 1, 1996, U.S. Provisional Application No. 60/026590, filed Sep. 20, 1996, and U.S. Provisional Application No. 60/026591, filed Sep. 20, 1996.

BACKGROUND OF THE INVENTION

This invention pertains to a process and catalyst for the direct oxidation of olefins, such as propylene, by oxygen to olefin oxides, such as propylene oxide.

Olefin oxides, such as propylene oxide, are used to alkoxylate alcohols to form polyether polyols, such as polypropylene polyether polyols, which find significant utility in the manufacture of polyurethanes and synthetic elastomers. Olefin oxides are also important intermediates in the manufacture of alkylene glycols, such as propylene glycol and dipropylene glycol, and alkanolamines, such as isopropanolamine, which are useful as solvents and surfactants.

Propylene oxide is produced commercially via the well-known chlorohydrin process wherein propylene is reacted with an aqueous solution of chlorine to produce a mixture of propylene chlorohydrins. The chlorohydrins are dehydrochlorinated with an excess of alkali to produce propylene oxide. This process suffers from the production of a low concentration salt stream. (See K. Weissermel and H. J. Arpe, *Industrial Organic Chemistry*, $2^{nd}$ ed., VCH Publishers, Inc., New York, N.Y., 1993, p. 264–265.)

Another well-known route to olefin oxides relies on the transfer of an oxygen atom from an organic hydroperoxide or peroxycarboxylic acid to an olefin. In the first step of this oxidation route, a peroxide generator, such as isobutane or acetaldehyde, is autoxidized with oxygen to form a peroxy compound, such as t-butyl hydroperoxide or peracetic acid. This compound is used to epoxidize the olefin, typically in the presence of a transition metal catalyst, including titanium, vanadium, molybdenum, and other heavy metal compounds or complexes. Along with the olefin oxide produced, this process disadvantageously produces equimolar amounts of a coproduct, for example an alcohol, such as t-butanol, or an acid, such as acetic acid, whose value must be captured in the market place. (See *Industrial Organic Chemistry*, ibid., p. 265–269.)

Although the direct oxidation of ethylene by molecular oxygen to ethylene oxide has been commercialized with a silver catalyst, it is known that the analogous direct oxidation of propylene exhibits a low selectivity to the olefin oxide. Disadvantageously large amounts of acrolein and oxygen-containing $C_{1-3}$ byproducts are produced, as taught in *Industrial Organic Chemistry*, ibid., p. 264. Some patents represented by U.S. Pat. Nos. 4,007,135 and 4,845,253, teach the use of metal-promoted silver catalysts for the oxidation of propylene with oxygen to propylene oxide. Among the metal promoters. disclosed are gold, beryllium, magnesium, calcium, barium, strontium, and the rare earth lanthanides. These promoted silver catalysts also exhibit low selectivities to the olefin oxide.

Alternatively, EP-A1-0,709,360 discloses a process of oxidizing an unsaturated hydrocarbon, such as propylene, with oxygen in the presence of hydrogen and a catalyst to form an epoxide, such as propylene oxide. Gold deposited on titanium dioxide, further immobilized on a carrier such as silica or alumina, is taught as the catalyst composition. The catalyst exhibits lower olefin oxide selectivity and less efficient hydrogen consumption when operated at higher temperatures. Additionally, the catalyst has a short run time.

PCT publication WO-A1-96/02323 discloses the oxidation of an olefin, including propylene, with oxygen in the presence of hydrogen and a catalyst to form an olefin oxide. The catalyst is a titanium or vanadium silicalite containing at least one platinum group metal, and optionally, an additional metal selected from gold, iron, cobalt, nickel, rhenium, and silver. The productivity of olefin oxide is low in this process.

In view of the above, a need continues to exist in the chemical industry for an efficient direct route to propylene oxide and higher olefin oxides from the reaction of oxygen with $C_3$ and higher olefins. The discovery of such a process which simultaneously achieves high selectivity to the olefin oxide at an economically advantageous conversion of the olefin would represent a significant achievement over the prior art. For commercial viability such a process would also require that the catalyst exhibit a long lifetime.

U.S. Pat. Nos. 4,839,327 and 4,937,219 represent additional art disclosing a composition comprising gold particles having a particle size smaller than about 500 Å immobilized on an alkaline earth oxide or titanium dioxide or a composite oxide of titanium dioxide with an alkaline earth oxide. A preparation of this composition involves deposition of a gold compound onto the alkaline earth oxide, titanium dioxide, or the composite oxide, followed by calcination so as to produce metallic gold of a particle size smaller than about 500 Å. This teaching is silent with respect to depositing the gold particles on a titanosilicate and to a process for producing olefin oxides.

SUMMARY OF THE INVENTION

This invention is a novel process of preparing an olefin oxide directly from an olefin and oxygen. The process comprises contacting an olefin having at least three carbon atoms with oxygen in the presence of hydrogen and in the presence of a catalyst under process conditions sufficient to produce the corresponding olefin oxide. The unique catalyst which is employed in the process of this invention comprises gold on a titanosilicate.

The novel process of this invention is useful for producing an olefin oxide directly from oxygen and an olefin having three or more carbon atoms. Unexpectedly, the process of this invention produces the olefin oxide in a remarkably high selectivity. Partial and complete combustion products, such as acrolein and carbon dioxide, which are found in large amounts in many prior art processes, are produced in lesser amounts in the process of this invention. Significantly, the process of this invention can be operated at a high temperature, specifically greater than about 120° C., while maintaining a high selectivity to olefin oxide. Operation at higher temperatures advantageously provides steam credits from the heat produced. Accordingly, the process of this invention can be integrated into a total plant design wherein the heat derived from the steam is used to drive additional processes, for example, the separation of the olefin oxide from water. Even more advantageously, since water is produced as a byproduct of this process, the hydrogen efficiency, as measured by the water to olefin oxide molar ratio, is good. Most advantageously, the process in its preferred embodiments exhibits an olefin conversion which is good.

In another aspect, this invention is a unique catalyst composition comprising gold on a titanosilicate.

The novel composition of this invention can be effectively used in the aforementioned direct oxidation of an olefin having three or more carbon atoms to the corresponding olefin oxide. Besides being active and highly selective for the olefin oxide, the catalyst exhibits evidence of a long lifetime. As a further advantage, when partially or completely spent, the catalyst is easy to regenerate. Accordingly, this unique catalyst exhibits highly desirable properties for the process of oxidizing propylene and higher olefins to their corresponding olefin oxides.

DETAILED DESCRIPTION OF THE INVENTION

The novel process of this invention comprises contacting an olefin having at least three carbon atoms with oxygen in the presence of hydrogen and an epoxidation catalyst under process conditions sufficient to prepare the corresponding olefin oxide. In one preferred embodiment, a diluent is employed with one or more of the reactants, as described in detail hereinafter. The relative molar quantities of olefin, oxygen, hydrogen, and optional diluent can be any which are sufficient to prepare the desired olefin oxide. In a preferred embodiment of this invention, the olefin employed is a $C_{3-12}$ olefin, and it is converted to the corresponding $C_{3-12}$ olefin oxide. In a more preferred embodiment, the olefin is a $C_{3-8}$ olefin, and it is converted to the corresponding $C_{3-8}$ olefin oxide. In a most preferred embodiment, the olefin is propylene, and the olefin oxide is propylene oxide.

The novel catalyst which is employed in the epoxidation process of this invention comprises gold on a titanosilicate. The titanosilicate is generally characterized as having a framework structure formed from $SiO_4^{4-}$ tetrahedra wherein a portion of the silicon atoms is replaced with titanium atoms. Preferably, the titanosilicate is a porous titanosilicate. In this preferred form, a series of pores or channels or cavities exists within the framework structure, thereby giving the titanosilicate its porous properties. A most preferred form of the titanosilicate is titanium silicalite-1 (TS-1) having a crystalline structure, as determined by X-ray diffraction (XRD), which is isomorphous to the structure of zeolite ZSM-5 and the pure silica form of ZSM-5 known as "silicalite". In a more preferred embodiment of the catalyst, the gold exists in the form of clusters having an average particle size of about 10 Å or greater, as determined by transmission electron microscopy (TEM).

Any olefin containing three or more carbon atoms can be employed in the process of this invention. Monoolefins are preferred, but compounds containing two or more olefins, such as dienes, can also be employed. The olefin can be a simple hydrocarbon containing only carbon and hydrogen atoms. Alternatively, the olefin can be substituted at any of the carbon atoms with an inert substituent. The term "inert", as used herein, requires the substituent to be substantially non-reactive in the process of this invention. Suitable inert substituents include, but are not limited to, halide, ether, ester, alcohol, and aromatic moieties, preferably, chloro, $C_{1-12}$ ether, ester, and alcohol moieties, and $C_{6-12}$ aromatic moieties. Non-limiting examples of olefins which are suitable for the process of this invention include propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methylpentene, ethylbutene, heptene, methylhexene, ethylpentene, propylbutene, the octenes, including preferably 1-octene, and other higher analogues of these; as well as butadiene, cyclopentadiene, dicyclopentadiene, styrene, a-methylstyrene, divinylbenzene, allyl chloride, allyl alcohol, allyl ether, allyl ethyl ether, allyl butyrate, allyl acetate, allyl benzene, allyl phenyl ether, allyl propyl ether, and allyl anisole. Preferably, the olefin is an unsubstituted or substituted $C_{3-12}$ olefin, more preferably, an unsubstituted or substituted $C_{3-8}$ olefin. Most preferably, the olefin is propylene. Many of the aforementioned olefins are available commercially; others can be prepared by chemical processes known to those skilled in the art.

The quantity of olefin employed in the process can vary over a wide range provided that the corresponding olefin oxide is produced. Generally, the quantity of olefin employed depends upon the specific process features, including for example, the design of the reactor, the specific olefin, and economic and safety considerations. Those skilled in the art can determine a suitable range of olefin concentrations for the specific process features desired. Generally, on a molar basis an excess of olefin is used relative to the oxygen, because this condition enhances the productivity to olefin oxide. Based on the process conditions disclosed herein, typically, the quantity of olefin is greater than about 1, preferably, greater than about 10, and more preferably, greater than about 20 mole percent, based on the total moles of olefin, oxygen, hydrogen, and optional diluent. Typically, the quantity of olefin is less than about 99, preferably, less than about 85, and more preferably, less than about 70 mole percent, based on the total moles of olefin, oxygen, hydrogen, and optional diluent.

Oxygen is also required for the process of this invention. Any source of oxygen is acceptable, including air and essentially pure molecular oxygen. Other sources of oxygen may be suitable, including ozone, and nitrogen oxides, such as nitrous oxide. Molecular oxygen is preferred. The quantity of oxygen employed can vary over a wide range provided that the quantity is sufficient for producing the desired olefin oxide. Ordinarily, the number of moles of oxygen per mole of olefin used in the feedstream is less than 1. Under these conditions the conversion of olefin and selectivity to olefin oxide are enhanced while the selectivity to combustion products, such as carbon dioxide, is minimized. Preferably, the quantity of oxygen is greater than about 0.01, more preferably, greater than about 1, and most preferably greater than about 5 mole percent, based on the total moles of olefin, hydrogen, oxygen, and optional diluent. Preferably, the quantity of oxygen is less than about 30, more preferably, less than about 25, and most preferably less than about 20 mole percent, based on the total moles of olefin, hydrogen, oxygen, and optional diluent. Above about 20 mole percent, the concentration of oxygen may fall within the flanunable range for olefin-hydrogen-oxygen mixtures.

Hydrogen is also required for the process of this invention. In the absence of hydrogen, the activity of the catalyst is significantly decreased. Any source of hydrogen can be used in the process of this invention, including for example, molecular hydrogen obtained from the dehydrogenation of hydrocarbons and alcohols. In an alternative embodiment of this invention, the hydrogen may be generated in situ in the olefin oxidation process, for example, by dehydrogenating alkanes, such as propane or isobutane, or alcohols, such as isobutanol. Alternatively, hydrogen may be used to generate a catalyst-hydride complex or a catalyst-hydrogen complex which can provide the necessary hydrogen to the process.

Any quantity of hydrogen can be employed in the process provided that the amount is sufficient to produce the olefin oxide. Suitable quantities of hydrogen are typically greater than about 0.01, preferably, greater than about 0.1, and more preferably, greater than about 3 mole percent, based on the total moles of olefin, hydrogen, oxygen, and optional diluent. Suitable quantities of hydrogen are typically less than about 50, preferably, less than about 30, and more preferably, less than about 20 mole percent, based on the total moles of olefin, hydrogen, oxygen, and optional diluent.

In addition to the above reagents, it may be desirable to employ a diluent with the reactants, although the use thereof is optional Since the process of this invention is exothermic, a diluent beneficially provides a means of removing and dissipating the heat produced. In addition the diluent provides an expanded concentration regime in which the reactants are non-flammable. The diluent can be any gas or liquid which does not inhibit the process of this invention. The specific diluent chosen will depend upon the manner in which the process is conducted. For example, if the process is conducted in a gas phase, then suitable gaseous diluents include, but are not limited to, helium, nitrogen, argon, methane, carbon dioxide, steam, and mixtures thereof. Most of these gases are essentially inert with respect to the process of this invention. Carbon dioxide and steam may not necessarily be inert, but may have a beneficial promoting effect. If the process is conducted in a liquid phase, then the diluent can be any oxidation stable and thermally stable liquid. Examples of suitable liquid diluents include aliphatic alcohols, preferably $C_{1-10}$ aliphatic alcohols, such as methanol and t-butanol; chlorinated aliphatic alcohols, preferably $C_{1-10}$ chlorinated alkanols, such as chloropropanol; chlorinated aromatics, preferably chlorinated benzenes, such as chlorobenzene and dichlorobenzene; as well as liquid polyethers, polyesters, and polyalcohols.

If used, the amount of diluent is typically greater than about 0, preferably greater than about 0.1, and more preferably, greater than about 15 mole percent, based on the total moles of olefin, oxygen, hydrogen, and diluent. The amount of diluent is typically less than about 90, preferably, less than about 80, and more preferably, less than about 70 mole percent, based on the total moles of olefin, oxygen, hydrogen, and diluent.

The aforementioned concentrations of olefin, oxygen, hydrogen, and diluent are suitably based on the reactor designs and process parameters disclosed herein. Those skilled in the art will recognize that concentrations other than the aforementioned ones may be suitably employed in other various engineering realizations of the process.

The unique catalyst which is beneficially employed in the process of this invention comprises gold on a titanosilicate. Surprisingly, gold in combination with a titanosilicate can exhibit catalytic oxidation activity and enhanced selectivity for olefin oxides. Preferably, the catalyst of this invention is essentially free of palladium. The term "essentially free" means that the concentration of palladium is less than about 0.01 weight percent, preferably, less than about 0.005 weight percent, based on the total weight of the catalyst. More preferably, the catalyst of this invention is essentially free of the Group VIII metals, which means that the total concentration of these metals is less than about 0.01 weight percent, preferably, less than about 0.005 weight percent, based on the total weight of the catalyst. The Group VIII metals include iron, cobalt, nickel, ruthenium, rhodium, palladium, osmium, iridium, and platinum.

The gold predominantly exists as elemental metallic gold, as determined by X-ray photoelectron spectroscopy or X-ray absorption spectroscopy, although higher oxidation states may also be present. Most of the gold appears from TEM studies to be deposited on the surface of the titanosilicate; however, the deposition of individual gold atoms or small gold clusters in the pores or on any extra-framework titania or the inclusion of ionic gold into the silica framework may also occur. Preferably, the gold is not associated with any extra-framework titania or titania added as a support, as analyzed by TEM. Typically, the average gold particle size (or diameter) is about 10 Å or greater, as measured by TEM. Preferably, the average gold particle size is greater than about 10 Å, more preferably, greater than about 12 Å, and most preferably, greater than about 25 Å. Preferably, the average gold particle size is less than about 500 Å, more preferably, less than about 200 Å, and most preferably, less than about 100 Å.

The titanosilicate is characterized by a framework structure formed from $SiO_4^{4-}$ tetrahedra and nominally $TiO_4^{4-}$ tetrahedra. The titanosilicate can be crystalline, which implies that the framework has a periodic regularity which is identifiable by X-ray diffraction (XRD). Alternatively, the titanosilicate can be amorphous, which implies a random or non-periodic framework which does not exhibit a well-defined XRD pattern.

Any titanosilicate can be employed in the catalyst of this invention. Preferably, the titanosilicate is porous, which means that within the titanosilicate framework structure there exists a regular or irregular system of pores or channels. Empty cavities, referred to as "cages", can also be present. The pores can be isolated or interconnecting, and they can be one, two, or three dimensional. Preferably, the pores are micropores or mesopores or some combination thereof. For the purposes of this invention, a micropore has a pore diameter (or critical dimension as in the case of a non-circular perpendicular cross-section) ranging from about 4 Å to about 20 Å, while a mesopore has a pore diameter or critical dimension ranging from greater than about 20 Å to about 200 Å. The combined volume of the micropores and the mesopores preferably comprises about 70 percent or greater of the total pore volume, and preferably, about 80 percent or greater of the total pore volume. The balance of the pore volume comprises macropores which have a pore diameter of greater than about 200 Å. These macropores will also include the void spaces between particles or crystallites.

The pore diameter (or critical dimension), pore size distribution, and surface area of the porous titanosilicate can be obtained from the measurement of adsorption isotherms and pore volume. Typically, the measurements are made on the titanosilicate in powder form using as an adsorbate nitrogen at 77 K or argon at 88 K and using any suitable adsorption analyzer, such as a Micromeritics ASAP 2000 instrument. Measurement of micropore volume is derived from the adsorption volume of pores having a diameter in the range from about 4 Å to about 20 Å. Likewise, measurement of mesopore volume is derived from the adsorption volume of pores having a diameter in the range from greater than about 20 Å to about 200 Å. From the shape of the adsorption isotherm, a qualitative identification of the type of porosity, for example, microporous or macroporous, can be made. Additionally, increased porosity can be correlated with increased surface area. Pore diameter (or critical dimension) can be calculated from the data using equations described by Charles N. Satterfield in Heterogeneous Catalysis in Practice, McGraw-Hill Book Company, New York, 1980, pp. 106–114, incorporated herein by reference.

Additionally, crystalline titanosilicates can be identified by X-ray diffraction(XRD), either by comparing the XRD pattern of the material of interest with a previously published standard or by analyzing the XRD pattern of a single crystal to determine framework structure, and if pores are present, the pore geometry and pore size.

Non-limiting examples of porous titanosilicates which are suitably employed in the process of this invention include porous amorphous titanosilicates; porous layered titanosilicates; crystalline microporous titanosilicates, such as titanium silicalite-1 (TS-1), titanium silicalite-2 (TS-2), titanosilicate beta (Ti-beta), titanosilicate ZSM-12 (Ti-ZSM-12) and titanosilicate ZSM-48 (Ti-ZSM-48); and mesoporous titanosilicates, such as Ti-MCM-41.

TS-1 possesses an MFI crystalline structure which is isomorphous to the crystalline structure of zeolite ZSM-5 and isomorphous to the structure of the pure silica form of ZSM-5 known as "silicalite. The three-dimensional framework structure of the pure silica "silicalite" is formally constructed from tetrahedral $SiO_4^{4-}$ units. In ZSM-5 some of the silica tetrahedra are replaced with $AlO_4^{5-}$ tetrahedra, and a cation, such as sodium ion, is needed to balance charge requirements. In TS-1 some of the silica tetrahedra are replaced with $TiO_4^{4-}$ tetrahedra. In this replacement, the overall charge remains electronically neutral and no additional cations are required. The pore structure of TS-1 comprises two interconnecting, roughly cylindrical, 10-ring pores of about 5 Å diameter. A 10-ring pore is formed from ten tetrahedral units. Titanium silicalite and its characteristic XRD pattern have been reported in U.S. Pat. No. 4,410,501, incorporated herein by reference. TS-1 can be obtained commercially, but it can also be synthesized following the methods described in U.S. Pat. No. 4,410,501. Other preparations have been reported by the following (incorporated herein by reference): A Tuel, *Zeolites*, 1996, 16, 108–117; by S. Gontier and A. Tuel, *Zeolites*, 1996, 16, 184–195; by A. Tuel and Y. Ben Taarit in *Zeolites*, 1993, 13, 357–364; by A. Tuel, Y. Ben Taarit and C. Naccache in *Zeolites*, 1993, 13, 454–461; by A. Tuel and Y. Ben Taarit in *Zeolites*, 1994, 14, 272–281; and by A. Tuel and Y. Ben Taarit in *Microporous Materials*, 1993, 1, 179–189.

TS-2 possesses an MEL topology which is isomorphous to the topology of the aluminosilicate ZSM-11. The pore structure of TS-2 comprises one three-dimensional, microporous, 10-ring system. TS-2 can be synthesized by methods described in the following references (incorporated herein by reference): J. Sudhakar Reddy and R. Kumar, *Zeolites*, 1992, 12, 95–100; by J. Sudhakar Reddy and R. Kumar, *Journal of Catalysis*, 1991, 130, 440–446; and by A. Tuel and Y. Ben Taarit, *Applied Catal. A, General*, 1993, 102, 69–77.

Ti-beta possesses a BEA crystalline structure which is isomorphous to the aluminosilicate beta. The pore structure of Ti-beta comprises two interconnecting 12-ring, roughly cylindrical pores of about 7 Å diameter. The structure and preparation of titanosilicate beta have been described in the following references, incorporated herein by reference: PCT patent publication WO 94/02245 (1994); M. A. Camblor, A. Corma, and J. H. Perez-Pariente, *Zeolites*, 1993, 13, 82–87; and M. S. Rigutto, R. de Ruiter, J. P. M. Niederer, and H. van Bekkum, *Stud. Surf. Sci. Cat.*, 1994, 84, 2245–2251.

Ti-ZSM-12 possesses an MTW crystalline structure which is isomorphous to the aluminosilicate ZSM-12. The pore structure of Ti-ZSM-12 comprises one, one-dimensional 12-ring channel system of dimensions 5.6×7.7 Å, as referenced by S. Gontier and A. Tuel, ibid., incorporated herein by reference.

Ti-ZSM-48 possesses a crystalline structure which is isomorphous to the aluminosilicate ZSM-48. The pore structure of Ti-ZSM-48 comprises a one-dimensional 10-ring channel system of dimensions 5.3 Å by 5.6 Å, as referenced by R. Szostak, *Handbook of Molecular Sieves*, Chapman & Hall New York, 1992, p. 551–553. Other references to the preparation and properties of Ti-ZSM-48 include C. B. Dartt, C. B. Khouw, H. X. Li, and M. E. Davis, *Microporous Materials*, 1994, 2, 425–437; and A. Tuel and Y. Ben Taarit, *Zeolites*, 1996, 15, 164–170, the aforementioned references being incorporated herein by reference.

Ti-MCM-41 is a hexagonal phase isomorphous to the aluminosilicate MCM-41. The channels in MCM-41 are one-dimensional with diameters ranging from about 28 Å to 100 Å. Ti-MCM-41 can be prepared as described in the following citations, incorporated herein by reference: S. Gontier and A. Tuel, *Zeolites*, 1996, 15, 601–610; and M. D. Alba, Z. Luan, and J. Klinowski, *J. Phys. Chem.*, 1996,100, 2178–2182.

The silicon to titanium atomic ratio (Si/Ti) of the titanosilicate can be any ratio which provides for an active and selective epoxidation catalyst in the process of this invention. A generally advantageous Si/Ti atomic ratio is equal to or greater than about 5/1, and preferably, equal to or greater than about 10/1. A generally advantageous Si/Ti atomic ratio is equal to or less than about 200/1, preferably, equal to or less than about 100/1. The Si/Ti atomic ratio defined hereinabove refers to a bulk ratio which includes the total of the framework titanium and the extra-framework titanium. At high. Si/Ti ratios, for example, about 100/1 or more, there may be little extra-framework titanium and the bulk ratio essentially corresponds to the framework ratio.

In one preferred embodiment of this invention, the catalyst is substantially free of the anatase phase of titanium dioxide, more preferably, substantially free of crystalline titanium dioxide, and most preferably, free of titanium dioxide. Crystalline titanium dioxide may be present, for example, as extra-framework titania or titania added as a carrier or support. Raman spectroscopy can be used to determine the presence of crystalline titanium dioxide. The anatase phase of titanium dioxide exhibits a characteristic strong, sharp Raman peak at about 147 $cm^{-1}$. The rutile phase exhibits Raman peaks at about 448 $cm^{-1}$ and about 612 $cm^{-1}$. The brookite phase, which usually is available only as a natural mineral, exhibits a characteristic peak at about 155 $cm^{-1}$. The rutile and brookite peaks have a lower intensity than the 147 $cm^{-1}$ peak of anatase. In the aforementioned more preferred embodiment of the catalyst, Raman peaks for the anatase, rutile, and brookite phases of titanium dioxide are essentially absent. When the catalyst exhibits essentially no detectable peaks at the aforementioned wavenumbers, then it is estimated that less than about 0.02 weight percent of the catalyst exists in the form of crystalline titanium dioxide. Raman spectra can be obtained on any suitable laser Raman spectrometer equipped, for example, with an argon ion laser tuned to the 514.5 nm line and having a laser power of about 90 to 100 mW measured at the sample.

The loading of the gold on the titanosilicate can be any loading which gives rise to the desired olefin oxide product. Generally, the gold loading is greater than about 0.01 weight percent, based on the total weight of gold and titanosilicate. Generally, the loading is less than about 20 weight percent. Preferably, the gold loading is greater than about 0.03, more preferably, greater than about 0.05 weight percent. Preferably, the gold loading is less than about 10.0, more preferably, less than about 5.0 weight percent.

The gold component can be deposited or supported on the titanosilicate by any method known in the art which provides for an active and selective catalyst. Non-limiting examples of known deposition methods include impregnation, ion-exchange, and deposition by precipitation. A preferred deposition method is disclosed by S. Tsubota, M. Haruta, T. Kobayashi, A. Ueda, and Y. Nakahara, "Preparation of Highly Dispersed Gold on Titanium and Magnesium Oxide," in *Preparation of Catalysts V*, G. Poncelet, P. A. Jacobs, P. Grange, and B. Delmon, eds., Elsevier Science Publishers B. V., Amsterdam, 1991, p. 695ff, incorporated herein by reference. This method involves contacting the titanosilicate with an aqueous solution of a soluble gold compound at a temperature and pH sufficient to precipitate the gold compound onto the titanosilicate. Non-aqueous solutions can also be employed. Thereafter, in the preferred method of this invention which is different from the aforementioned reference, the gold/titanosilicate composite is not washed or is lightly washed, with preferably no more than about 100 ml wash liquid per gram composite. Then, the composite is calcined or reduced at a temperature sufficient to reduce the gold substantially to metallic gold having an average particle size between about 10 Å and about 500 Å.

For aqueous solvents, any water soluble gold compound can be used, such as chloroauric acid, sodium chloroaurate, potassium chloroaurate, gold cyanide, potassium gold cyanide, and diethylamine auric acid trichloride. Typically, the molarity of the soluble gold compound ranges from about 0.001 M to the saturation point of the soluble gold compound, preferably, from about 0.005 M to about 0.5 M. The desired quantity of titanosilicate is added to the solution, or vice versa; and the pH is adjusted to between about 5 and about 11, preferably, between about 6 and about 9, with any suitable base, such as a Group 1 hydroxide or carbonate, preferably, sodium hydroxide, sodium carbonate, potassium carbonate, cesium hydroxide, and cesium carbonate. Thereafter, the mixture is stirred under air at a temperature between about 20° C. and about 80° C. for a time ranging from about 1 hour to about 15 hours. At the end of this period, the solids are recovered and optionally washed with water, the water optionally containing promoter metal salts, described hereinbelow, preferably at a pH between about 5 and 11. Typically thereafter, the solids are dried under air at a temperature between about 80° C. and about 110° C. The solid is then calcined under air, or calcined in a reducing atmosphere, such as hydrogen, or heated in an inert atmosphere, such as nitrogen, at a temperature between about 250° C. and about 800° C. for a time from about 1 hour to about 24 hours to form a titanosilicate having metallic gold thereon.

Optionally, the catalyst of this invention can contain a promoter metal or a combination of promoter metals. Any metal ion having a valence between +1 and +7 which enhances the productivity of the catalyst in the oxidation process of this invention can be employed as a promoter metal. Factors contributing to increased productivity of the catalyst include increased conversion of the olefin, increased selectivity to the olefin oxide, decreased production of water, and increased catalyst lifetime. Non-limiting examples of suitable promoter metal include the metals of Groups 1 through 12 of the Periodic Table of the Elements, as well as the rare earth lanthanides and actinides, as referenced in the CRC *Handbook of Chemistry and Physics*, 75$^{th}$ ed., CRC Press, 1994. Preferably, the promoter metal is selected from Group 1 metals of the Periodic Table including lithium, sodium, potassium, rubidium, and cesium; from Group 2 metals, including beryllium, magnesium, calcium, strontium, and barium; from the lanthanide rare earth metals, including cerium, praseodymium, neodymium, promethium, samarium, europium, gadolinium, terbium, dysprosium, holmium, erbium, thulium, ytterbium, and lutetium; and the actinide metals, specifically, thorium and uranium, or from a combination of these metals. More preferably, the promoter metal is magnesium, calcium, barium, erbium, lutetium, lithium, potassium, rubidium, cesium, or a combination thereof. In another preferred embodiment, the promoter metal excludes palladium, and even more preferably, excludes a Group VIII metal, including, iron, cobalt, nickel ruthenium, rhodium, palladium, osmium, iridium, and platinum. As used herein the word "excludes" means that the concentration of the metal is less than about 0.01, preferably, less than about 0.005 weight percent, based on the total weight of the catalyst.

If one or more promoter metals are used as described hereinabove, then the total quantity of promoter metal(s) generally is greater than about 0.01, preferably, greater than about 0.10, and more preferably, greater than about 0.15 weight percent, based on the total weight of the catalyst. The total quantity of promoter metal(s) is generally less than about 20, preferably, less than about 15, and more preferably, less than about 10 weight percent, based on the total weight of the catalyst.

The promoter metal(s) can be deposited or supported onto the titanosilicate simultaneously with the gold particles, or alternatively, in a separate step either before or after the gold is deposited or supported. Generally, the promoter metal is deposited from an aqueous or organic solution containing a soluble promoter metal salt. Any salt of the promoter metal which has adequate solubility can be used; for example, the metal nitrates, carboxylates, and halides, preferably the nitrates, are suitable. If an organic solvent is employed, it can be any of a variety of known organic solvents, including, for example, alcohols, esters, ketones, and aliphatic and aromatic hydrocarbons. Ordinarily, the titanosilicate is contacted with the solution of the promoter metal salt under conditions which are similar to those used for contacting the titanosilicate with the gold solution. After the promoter metal is deposited, washing is optional. If done to excess, washing can leach at least a portion of the promoter metal out of the catalyst. Afterwards, calcination under air or under a reducing atmosphere or heating in an inert gas is conducted in a manner similar to that described hereinabove for the gold deposition.

Optionally, the catalyst of this invention can be extruded with, bound to, or supported on a second support, such as silica, alumina, an aluminosilicate, magnesia, titania, carbon, or mixtures thereof. The second support may function to improve the physical properties of the catalyst, such as, the strength or attrition resistance, or to bind the catalyst particles together. Generally, the quantity of second support ranges from about 0 to about 95 weight percent, based on the combined weight of the catalyst and second support. It is noted that although the catalyst of this invention can be physically mixed or extruded with titania or bound to titania as a second support, in a preferred embodiment the catalyst is substantially free of the anatase phase of titanium dioxide, more preferably free of crystalline titanium dioxide, as noted hereinabove. If titania is used as a second support, however, note that its presence may interfere with the analytical identification of the catalyst. In this instance especially, analysis of the catalyst should be made in the absence of the second support.

The process of this invention can be conducted in a reactor of any conventional design suitable for gas or liquid phase processes. These designs broadly include batch, fixed-bed, transport bed, fluidized bed, moving bed, trickle bed, and shell and tube reactors, as well as continuous and intermittent flow and swing reactor designs. Alternatively, the process may be conducted in two-steps wherein the catalyst is first contacted with oxygen and thereafter the oxygenated catalyst is contacted with a mixture of propylene and hydrogen. Preferably, the process is conducted in the gas phase and the reactor is designed with heat transfer features for the removal of the heat produced. Preferred reactors designed for these purposes include fixed-bed, shell and tube, fluidized bed, and moving bed reactors, as well as swing reactors constructed from a plurality of catalyst beds connected in parallel and used in an alternating fashion.

The process conditions for the direct oxidation described herein can vary considerably over a nonflammable and flammable regime. It is beneficial, however, to recognize the conditions which distinguish between nonflammable and flammable mixtures of the olefin, hydrogen, and oxygen. Accordingly, a phase diagram can be constructed or consulted which for any given process temperature and pressure shows the flammable and non-flammable range of reactant compositions, including the diluent, if used. The more preferred reactant mixtures specified hereinabove are believed to lie outside the flammable regime when the process is operated at the more preferred temperatures and pressures specified hereinbelow. Nevertheless, operation within the flammable regime is possible, as designed by one skilled in the art.

Usually, the process is conducted at a temperature which is greater than about ambient, taken as 20° C., preferably, greater than about 70° C., more preferably greater than about 120° C. Usually, the process is conducted at a temperature less than about 250° C., preferably less than about 225° C., more preferably, less than about 200° C. Preferably, the pressure ranges from about atmospheric to about 400 psig (2758 kPa), more preferably, from about 150 psig (1034 kPa) to about 250 psig (1724 kPa).

In flow reactors the residence time of the reactants and the molar ratio of reactants to catalyst will be determined by the space velocity. For a gas phase process the gas hourly space velocity (GHSV) of the olefin can vary over a wide range, but typically is greater than about 10 ml olefin per ml catalyst per hour ($hr^{-1}$), preferably greater than about 100 $hr^{-1}$, and more preferably, greater than about 1,000 $hr^{-1}$. Typically, the GHSV of the olefin is less than about 50,000 $hr^{-1}$, preferably, less than about 35,000 $hr^{-1}$, and more preferably, less than about 20,000 $hr^{-1}$. Likewise, for a liquid phase process the weight hourly space velocity (WESV) of the olefin component may vary over a wide range, but typically is greater than about 0.01 g olefin per g catalyst per hour ($hr^{-1}$), preferably, greater than about 0.05 $hr^{-1}$, and more preferably, greater than about 0.1 $hr^{-1}$. Typically, the WHSV of the olefin is less than about 100 $hr^{-1}$, preferably, less than about 50 $hr^{-1}$, and more preferably, less than about 20 $hr^{-1}$. The gas and weight hourly space velocities of the oxygen, hydrogen, and diluent components can be determined from the space velocity of the olefin taking into account the relative molar ratios desired.

When an olefin having at least three carbon atoms is contacted with oxygen in the presence of hydrogen and the catalyst described herein-above, the corresponding olefin oxide (epoxide) is produced in good productivity. The most preferred olefin oxide produced is propylene oxide.

The conversion of olefin in the process of this invention can vary depending upon the specific process conditions employed, including the specific olefin, temperature, pressure, mole ratios, and form of the catalyst. As used herein, the term "conversion" is defined as the mole percentage of olefin which reacts to form products. Generally, the conversion increases with increasing temperature and pressure and decreases with increasing gas hourly space velocity. Typically, an olefin conversion of greater than about 0.05 mole percent is achieved. Preferably, the olefin conversion is greater than about 0.2 percent.

Likewise, the selectivity to olefin oxide can vary depending upon the specific process conditions employed. As used herein, the term "selectivity" is defined as the mole percentage of reacted olefin which forms a particular product, desirably the olefin oxide. Generally, the selectivity to olefin oxide will decrease with increasing temperature and increase with increasing space velocity. The process of this invention produces olefin oxides in unexpectedly high selectivity. A typical selectivity to olefin oxide in this process is greater than about 50, preferably, greater than about 70, and more preferably, greater than about 90 mole percent. A selectivity to propylene oxide of greater than about 99 mole percent at 50° C. has been achieved. Even at 165° C. the selectivity to propylene oxide is surprisingly high, between about 85 and 95 mole percent.

Advantageously, the hydrogen efficiency in the process of this invention is satisfactory. Some additional hydrogen may be burned directly to form water. Accordingly, it is desirable to achieve a water/olefin oxide molar ratio as low as possible. In the process of this invention, the water/olefin oxide molar ratio is typically greater than about 2/1, but less than about 15/1, and preferably, less than about 10/1, and more preferably, less than about 7/1.

The catalyst of this invention exhibits evidence of a long lifetime. The term "lifetime" as used herein refers to the time measured from the start of the oxidation process to the point at which the catalyst after regeneration has lost sufficient activity so as to render the catalyst useless, particularly commercially useless. As evidence of its long lifetime, the catalyst remains active for long periods of time with little deactivation. Typically, a run time greater than about 100 hours without catalyst deactivation has been achieved in a fixed bed reactor. In a preferred mode, a run time greater than about 550 hours without catalyst deactivation has been achieved. The preferred run time between regenerations will depend upon the reactor design and may range from minutes for transport bed reactors to several months for fixed bed reactors. As further evidence of its longevity, the catalyst of this invention can be regenerated through multiple cycles without substantial loss in catalyst activity or selectivity.

When its activity has decreased to an unacceptably low level, the catalyst of this invention can be easily regenerated. Any catalyst regeneration method generally known to those skilled in the art can be used with the catalyst of this invention provided that the catalyst is reactivated for the oxidation process described herein. One suitable regeneration method comprises heating the deactivated catalyst at a temperature between about 150° C. and about 500° C. under an atmosphere of a regeneration gas containing hydrogen and/or oxygen and optionally an inert gas. A preferred regeneration temperature varies between about 200° C. and about 400° C. The amounts of hydrogen and/or oxygen in the regeneration gas can be any which effectively regenerates the catalyst. Preferably, the hydrogen and/or oxygen comprises from about 2 to about 100 mole percent of the regeneration gas. Suitable inert gases are non-reactive and include, for example, nitrogen, helium, and argon. The regeneration cycle time, that is the time during which the catalyst is being regenerated, can range from as little as about 2 minutes to as long as several hours, for example, about 20 hours at the lower regeneration temperatures. In an alternative embodiment, water is beneficially added to the regeneration gas in an amount preferably ranging from about 0.01 to about 100 mole percent.

The invention will be further clarified by a consideration of the following examples, which are intended to be purely exemplary of the use of the invention. Other embodiments of the invention will be apparent to those skilled in the art from a consideration of this specification or practice of the invention as disclosed herein. Unless otherwise noted, all percentages are given on a weight percent basis.

Preparation of Titanium Silicalite TS-1 Having Si/Ti=100

Tetraethylorthosilicate (Fisher TEOS, 832.5 g) was weighed into a 4 liter stainless steel beaker and sparged with nitrogen gas for 30 minutes. Titanium n-butoxide (DuPont, Ti(O-n-Bu)$_4$) was injected from a syringe into the silicate. The weight of the titanium n-butoxide which was added to the TEOS was 14.07 g, taken by difference. A clear yellow solution was formed. The solution was heated and stirred under nitrogen for about 3 hr. The temperature varied from 50° C. to 130° C. The solution was then chilled in an ice bath.

A 40 percent aqueous solution of tetrapropylammonium hydroxide (TPAOH, 710.75 g) was weighed into a polyethylene bottle, which was capped and placed in an ice bath. The TPAOH was added dropwise to the chilled TEOS solution with vigorous stirring by an overhead stirrer. After one-half of the TPAOH had been added, the TEOS solution was cloudy and began to thicken. Within five minutes the solution froze completely. At this point the remainder of the TPAOH was added, the gel was broken up with a spatula, and stirring was resumed. Deionized water (354 g) was added, and the solution was warmed to room temperature. After 5 hr the solids had largely dissolved, and an additional quantity of deionized water (708 g) was added. Stirring was continued overnight yielding a clear yellow synthesis gel containing no solids.

The synthesis gel was poured into a 1 gallon (3.785 liters) stainless steel autoclave and sealed. The autoclave was heated to 120° C. and then gradually to 160° C. where it was kept for 6 days. The reactor contents were stirred at all times. At the end of the reaction period, the autoclave was cooled and a milky white suspension was recovered. The solids were recovered, washed, centrifuged, and resuspended in deionized water. The solids were filtered, dried at room temperature, heated slowly to 550° C, and calcined thereat for 8 hr. The solid was identified as having an MFI structure, as determined by XRD. Raman spectra did not reveal any known crystalline titania phase. A Si/Ti atomic ratio of 100 was found, as measured by X-ray fluorescence (XRF). Yield of titanium silicalite-1: 106 g.

EXAMPLE 1
Preparation of Epoxidation Catalyst

Titanium silicalite TS-1 (10.042 g) having a Si/Ti atomic ratio of 100, prepared as described hereinabove, was added to an aqueous solution of chloroauric acid, $HAuCl_4 \cdot 3H_2O$ (0.4829 g in 50 ml water). The pH was adjusted to between 7 and 8 by adding sodium carbonate. Magnesium nitrate, $Mg(NO_3)_2 \cdot 6H_2O$ (1.97 g), was added as was more sodium carbonate until the pH was between 7 and 8. The total amount of sodium carbonate used was 0.62 g. The mixture was stirred overnight. A solid product was filtered, and the filtercake was washed 3 times with 150 ml of water. The wet filtercake was dried at 100° C. for 2 hr. The dried solid was heated over an 8 hr period to 400° C. and then calcined under air at 400° C. for 5 hr to yield an epoxidation catalyst comprising gold on TS-1. Catalyst composition as determined by neutron activation analysis (NAA) was the following: Au, 1.07, Si 41.0, Ti 0.77, Mg 0.21, and Na 0.31 percent. The average gold particle size was 35 Å, as determined by TEM.

EXAMPLE 2
Oxidation of Propylene to Propylene Oxide

The epoxidation catalyst of Example 1 was tested in the direct oxidation of propylene to propylene oxide. The catalyst (5 cc) was loaded into a 10 cc fixed-bed, continuous flow reactor with flows of helium, oxygen, hydrogen, and propylene. Total flow rate was 150 cc/min (or GHSV 1,800 hr$^{-1}$). Feedstream composition was 5.0 mole percent hydrogen, 10.5 mole percent oxygen, and 53.6 mole percent propylene, the balance being helium. Propylene, oxygen and helium were used as pure streams; hydrogen was mixed with helium in a 20 $H_2$/80 He (v/v) mixture. Pressure was atmospheric; reactor temperature ranged from 50° C. to 165° C. Products were analyzed using an on-line gas chromatograph (Chrompack™ Poraplot™ S column, 25 m) with the results shown in Table 1.

TABLE 1

Direct Oxidation of Propylene (PP) to Propylene Oxide (PO) Using Gold on TS-1 (Si/Ti = 100)[a]

| Time (hr) | T (° C.) | Conv PP (mol %) | Sel PO (mol %) | $H_2O$/PO |
|---|---|---|---|---|
| 0.5 | 50 | 0.008 | 57.1 | — |
| 1 | 50 | 0.019 | 84.8 | — |
| 3 | 50 | 0.064 | 96.8 | — |
| 7 | 50 | 0.123 | 98.3 | 5.59 |
| 11 | 50 | 0.164 | 99.3 | 2.85 |
| 14 | 50 | 0.160 | 99.0 | 2.88 |
| 19.5 | 60 | 0.211 | 98.8 | 3.40 |
| 22 | 70 | 0.287 | 98.3 | 4.06 |
| 24 | 80 | 0.366 | 97.6 | 4.67 |
| 40 | 80 | 0.200 | 97.5 | 5.26 |
| 60 | 90 | 0.180 | 96.1 | 7.74 |
| 73 | 110 | 0.264 | 91.8 | 12.20 |
| 119[b] | 110 | 0.128 | 95.0 | 8.32 |
| 140 | 120 | 0.108 | 93.5 | 8.85 |
| 176[c] | 150 | 0.289 | 88.2 | 20.50 |
| 208 | 165 | 0.423 | 84.6 | 18.00 |
| 258 | 165 | 0.444 | 86.0 | 13.17 |
| 275 | 165 | 0.446 | 85.5 | 15.27 |

[a]Feedstream (mol %): 5.0% $H_2$, 10.5% $O_2$, 53.6% propylene, balance helium; flow 150 cc/min; pressure atmospheric
[b]How increased at 119 hr to 300 cc/min.
[c]Flow increased at 176 hr to 400 cc/min.

It is seen that a composition comprising gold with magnesim on TS-1 having a Si/Ti molar ratio of 100 is capable of catalyzing the direct oxidation of propylene to propylene oxide. Activity increases with increasing temperature with a propylene conversion of 0.20 mole percent at 110° C. Selectivity to propylene oxide reaches a maximum of over 99 mole percent. The water/propylene oxide molar ratio is good, and the catalyst remains active at 275 hr.

Preparation of Titanium Silicalite TS-1 having Si/Ti=27

Tetraethylorthosilicate (Fisher TEOS, 1250 g) was weighed into a 3 liter Erlenmeyer flask and sparged with nitrogen gas for 30 minutes. Titanium n-butoxide (DuPont, Ti(O-n-Bu)$_4$, 51.2 g) was injected from a syringe into the TEOS with vigorous stiring. The flask was placed in a 50° C. water bath, stirred for 1 hr, and left to stand for about 60 hr with a nitrogen pad.

A 40 percent solution of tetrapropylammonium hydroxide (Sachem TPAOH, 1069.7 g) was added to deionized water (540 g) in a 2 liter beaker and chilled in an ice bath. The TEOS was also chilled in an ice bath. When both solutions were chilled below 10° C., the TEOS solution was transferred to a 4 liter stainless steel beaker equipped with an overhead stirrer. The TPAOH solution was added dropwise by means of an addition funnel. Addition was completed over 5 hr to form a clear yellow synthesis gel.

The synthesis gel was poured into a 1 gallon (3.785 liters) stainless steel autoclave and sealed. The autoclave was heated to 100° C. for about 2 hr and then to 140° C. for about 2 hr and then to 160° C. for 6 days. The reactor contents were stirred at all times. At the end of the reaction period the autoclave was cooled and a milky white suspension was recovered. The solids were recovered, washed, centrifuged, and resuspended in deionized water. The washing was repeated three times until the pH of the wash water was below pH 9. The solids were dried at 65° C. overnight to form white cakes, which were crushed to pass a 20 mesh sieve. This solid was heated to 500° C. over 8 hr and then calcined under air at 500° C. for 2 hr. The solid was identified by XRD to have an MFI structure. Raman spectra revealed titania in the anatase phase (about 50 percent of the total weight of titanium). The Si/Ti atomic ratio was determined to be 27 by XRF. Yield: 175.5 g.

EXAMPLE 3
Preparation of Epoxidation Catalyst

A catalyst composition comprising gold on TS-1 having a Si/Ti atomic ratio of 27 was prepared according to the method of Example 1, with the exception that the following amounts of reagents were used: TS-1, 10.07 g; chloroauric acid, 0.4876 g in 50 ml water; sodium carbonate 0.60 g total; and magnesium nitrate, 1.98 g. Catalyst composition as determined by NAA was the following: Au 0.71, Si 41.9, Ti 2.39, Mg 0.18, and Na 0.24 percent. The average gold particle size was 18 Å, as measured by TEM.

EXAMPLE 4
Oxidation of Propylene to Propylene Oxide

The epoxidation catalyst of Example 3 was tested in the direct oxidation of propylene to propylene oxide in a manner similar to that described in Example 2 with the results shown in Table 2.

TABLE 2

Direct Oxidation of Propylene (PP) to Propylene Oxide (PO) Using Au/TS-1 (Si/Ti = 27)[a]

| Time (hr) | T (° C.) | Conv PP (mol %) | Sel PO (mol %) | H$_2$O/PO |
|---|---|---|---|---|
| 0.5 | 35 | 0.007 | 52.9 | — |
| 1.0 | 50 | 0.019 | 93.8 | — |
| 1.5 | 60 | 0.168 | 99.0 | 5.43 |
| 4 | 60 | 0.173 | 99.3 | 3.17 |
| 6 | 60 | 0.149 | 99.5 | 2.52 |
| 8 | 60 | 0.132 | 99.4 | 2.85 |
| 94 | 60 | 0.042 | 100 | 3.49 |
| 96 | 70 | 0.067 | 99.4 | 3.55 |
| 101 | 80 | 0.109 | 99.3 | 3.29 |
| 117 | 80 | 0.088 | 99.1 | 3.46 |
| 122 | 90 | 0.131 | 99.1 | 3.62 |
| 150 | 110 | 0.175 | 98 | 5.39 |
| 240 | 110 | 0.120 | 97 | 7.01 |
| 250 | 140 | 0.25 | 97 | 9.19 |
| 275[b] | 150 | 0.25 | 97 | 10.48 |
| 300[c] | 165 | 0.34 | 95 | 9.33 |

[a]Feedstream (mol %): 5.0% H$_2$, 10.5% O$_2$, 53.6% propylene, balance helium; flow 150 cc/min; pressure atmospheric
[b]How increased at 275 br to 300 cc/min.
[c]Flow increased at 300 hr to 500 cc/min.

It is seen that a composition comprising gold and magnesium on TS-1 having a Si/Ti molar ratio of 27 is capable of catalyzing the direct oxidation of propylene to propylene oxide. Propylene conversion increases with increasing temperature to a value of 0/25 mole percent at 140° C. Selectivity to propylene oxide remains over 90 mole percent and reaches a maximum of nearly 100 percent. The water/propylene oxide molar ratio is good, and the catalyst remains active at 300 hr.

EXAMPLES 5(a) and 5(b)
Preparation of Catalysts and Evaluation in the Oxidation of Propylene to Propylene Oxide.

Two catalysts were prepared as follows. Chloroauric acid was dissolved in water (50 g). TS-1 having a Si/Ti of 27, prepared hereinabove, was added to the solution with stirring. In sample 5(a) sodium was added as a promoter. In sample 5(b) erbium and sodium were added as promoters. The mixtures were stirred for 1 hr. Sodium carbonate was added to each mixture to adjust the pH to between 7.0 and 7.6. The solution was stirred for 1.0 hr, and the pH was readjusted if needed with sodium carbonate. The mixture was stirred overnight. A solid was filtered from each sample and washed three times with water (150 cc per wash). The solid was dried at 110° C. for 1 hr in air, crushed lightly to break big particles, then calcined in air at 120° C. for 3 hr. Then, the solid was heated to 400° C. over 8 hr and held at 400° C. for 5 hr. Afterwards, the solid was cooled to 350° C. for 1 hr and then to room temperature to yield a catalyst comprising gold supported on TS-1. The amounts of reagents used are listed for each catalyst.

Ex. 5(a): chloroauric acid, 0.217 g; TS-1, 10.040 g; sodium carbonate, 0.218 g;

Ex. 5(b): chloroauric acid, 0.134 g; TS-1, 5.054 g; erbium nitrate, 1.048 g; sodium carbonate, 0.596 g.

The average size of the gold particles was 30 Å for catalyst 5(a) and 35 Å for catalyst 5(b), as measured by TEM. Gold loading was about 0.7 percent for both catalysts; erbium loading was 6.5 percent, as determined by XRF.

The catalysts were evaluated in the oxidation of propylene to propylene oxide in a manner similar to that described in Example 2, with the exception that the feedstream comprised 10 mole percent hydrogen, 10 mole percent oxygen, 30 mole percent propylene, and the balance helium. Results are set forth in Table 3.

TABLE 3

Direct Oxidation of Propylene (PP) to Propylene Oxide (PO) On Au/TS-1 Catalysts[a]

| Ex. | Metal Promoter Other Than Na | T (° C.) | Time on Stream (hr) | Conv PP (mol %) | Sel PO (mol %) |
|---|---|---|---|---|---|
| 5(a) | None | 70 | 15 | 0.09 | 97.5 |
| " | " | 110 | 18 | 0.25 | 95.6 |
| " | " | 140 | 130 | 0.40 | 92.0 |
| 5(b) | Er (6.5%) | 70 | 15 | 0.15 | 98.2 |
| " | " | 110 | 18 | 0.44 | 96.7 |
| " | " | 140[b] | 130 | 0.45 | 92.0 |

[a]Feedstream (mol %): 10% $H_2$, 10% $O_2$, 30% propylene, balance helium; flow 150 cc/min, pressure atmospheric; Catalyst 5(a), 10 cc; Catalyst 5(b), 5 cc.
[b]Flow increased at 140° C. to 200 cc/min.

Both catalysts are seen to catalyze the direct oxidation of propylene to propylene oxide. When Example 5(a) is compared with Example 5(b) under identical process conditions, it is seen that the catalyst with the erbium promoter has a higher conversion at about the same selectivity. In Example 5(b) conversion reaches 0.44 mole percent at a selectivity to propylene oxide of 96.7 mole percent.

EXAMPLE 6

Evaluation of Regenerated Catalysts

The used catalysts of Examples 5(a) and 5(b) were removed from the reactors and put into an air oven at 400° C. and stirred every 30 min for a total of 2 hr to yield regenerated catalysts which were evaluated in the oxidation of propylene to propylene oxide as shown in Table 4, Examples 5(a)-1 and 5(b)-1. The catalysts were regenerated a second time at 220° C. in 10 mole percent oxygen in helium and then cooled to 130° C. where they were evaluated in the oxidation process, as shown in Table 4, Examples 5(a)-2 and 5(b)-2. The catalysts were regenerated a third time at 250° C. in 10 mole percent oxygen in helium and then cooled to 130° C. where they were evaluated in the oxidation process, as shown in Table 4, Example 5(a)-3 and 5(b)-3. The erbium promoted catalyst was heated to 385° C. overnight in the oxygen/helium mixture and evaluated in the oxidation process as shown in Table 4, Example 5(b)-4.

TABLE 4

Use of Regenerated Catalysts in Direct Oxidation of Propylene(PP) to Propylene Oxide (PO)[a]

| Ex. | T (° C.) | Time on Stream (hr) | Conv PP (mol %) | Sel. PO (mol %) |
|---|---|---|---|---|
| 5(a)-1 | 110 | 2 | 0.18 | 91 |
| " | 110 | 8 | 0.16 | 93 |
| " | 110 | 12 | 0.15 | 93 |
| " | 130 | 24 | 0.20 | 92 |
| 5(a)-2 | 130 | 4 | 0.20 | 94 |
| 5(a)-3 | 130 | 4 | 0.24 | 90 |
| 5(b)-1 | 110 | 2 | 0.58 | 97 |
| " | 110 | 8 | 0.30 | 97 |
| " | 110 | 12 | 0.22 | 97 |
| " | 130 | 24 | 0.27 | 96 |
| 5(b)-2 | 130 | 4 | 0.28 | 95 |
| 5(b)-3 | 130 | 4 | 0.26 | 89 |
| 5(b)-4 | 130 | 0.5 | 0.83 | 90 |
| " | 130 | 3.5 | 0.53 | 92 |
| " | 130 | 8 | 0.46 | 93 |

[a] Feedstream (mol %): 10% $H_2$, 10% $O_2$, 30% propylene, balance helium; flow 150 cc/min, pressure atmospheric.

It is seen in Table 4 catalysts regenerated up to four times continue to exhibit significant activity high propylene oxide selectivity.

EXAMPLE 7

Catalyst Preparation and Epoxidation Process

A mesoporous titanosilicate, similar to Ti-MCM-41, was obtained and was chatacterized as follows. The presence of Ti and Si was determined by XRF. The XRD pattern of the calcined material showed a single intense peak at about d=40 Å. The surface area of the material was determined by argon adsorption to be 1543 $m^2/g$ with a uniform pore-size distribution centered at about 30 Å.

The mesoporous titanosilicate (10 g) was added to water (700 ml) and the mixture was heated to 80° C. A solution consisting of water (150 ml) and chloroauric acid (0.225 g) was added to the mixture containing the mesoporous titanosilicate. A solution consisting of water (50 ml) and calcium nitrate (20 g) was added to the mixture. The pH was raised to 7.5 with ammonium hydroixde, and the mixture was stirred for 2 hr. The solids were filtered and washed with copious amounts of water. The washed solids were calcined in 8 hr to 350° C., then held at 350° C. in 5 mole percent hydrogen in helium for 3 hr to yield a catalyst comprising gold and calcium on a mesoporous titanosilicate. Gold loading was 1 percent, and gold average particle size was 30 Å.

The catalyst (5 g) was tested in the direct oxidation of propylene to propylene oxide in a manner similar to that described in Example 2 with the results shown in Table 5.

TABLE 5

Propylene (PP) Oxidation to Propylene Oxide (PO) Using Au and Ca on Mesoporous Titanosilicate[a]

| T (° C.) | Flow (cc/min) | Run Time (hr) | Conv PP (mol %) | Sel PO (mol %) |
|---|---|---|---|---|
| 110 | 100 | 20 | 0.07 | 90 |
| 120 | 75 | 45 | 0.08 | 80 |
| 130 | 150 | 68 | 0.08 | 80 |
| 140 | 150 | 86 | 0.09 | 78 |
| 145 | 150 | 168 | 0.10 | 79 |
| 150 | 150 | 203 | 0.10 | 78 |

[a]Feedstream (mol %): 10% $H_2$, 10% $O_2$, 30% propylene, balance helium, pressure atmospheric.

It is seen that a composition comprising gold and calcium on a mesoporous titanosilicate can catalyze the direct oxidation of propylene to propylene oxide. At 145° C. the conversion is 0.10 mole percent and the propylene oxide selectivity is 79 mole percent.

Preparation of Ti-Beta

Titanium tetrachloride (4.00 g) was added with string to ethanol (10.0 ml) under a nitrogen atmosphere. The resulting solution was added to colloidal silica (Ludox HS-40, 40 percent $SiO_2$, 53.12 g) and the mixture was stirred until a clear sol was obtained. Sodium hydroxide (5.34 g) was dissolved in water (204.14 g). Sodium aluminate (3.23 g, MCB-Merck, 47 percent $Al_2O_3$, 28 percent $Na_2O$, 25 percent $H_2O$) was added to the hydroxide solution and stirred until dissolved. Tetraethylammonium hydroxide solution (40 percent) was added to the sodium hydroxide-sodium alminate solution. The sol containing the titanium and silica sources was added to the hydroxide-aluminate solution with vigorous stirring. The resulting mixture was stirred and aged for 8 hr at room temperature, then charged into a stirred reactor (450 ml) and aged therein at 165° C. for 3 days. At the end of the crystallization period, the reactor was quenched in cold water. The product was filtered, washed with water until the washings were at pH 8, and dried overnight at room temperature. The dried material was calcined in air by heating to 500° C. over 5 hr and then holding at 500° C. for 4 hr. The calcined material was a highly crystalline form of beta, as determined by XRD. The presence of Si and Ti were determined by XRF.

EXAMPLE 8
Catalyst Preparation and Epoxidation Process

A catalyst was prepared comprising gold (1 percent) and calcium on Ti-beta. The catalyst was prepared as in Example 7 with the exception that Ti-beta was used in place of the mesoporous titanosilicate. The catalyst was tested in the direct oxidation of propylene in a manner similar to that described in Example 2 with the results shown in Table 6.

TABLE 6

Propylene (PP) Oxidation to Propylene Oxide (PO) Using Au and Ca on Ti-Beta[a]

| T (° C.) | Run Time (hr) | Conv PP (mol %) | PO Sel (mol %) |
|---|---|---|---|
| 130 | 69 | 0.025 | 75 |
| 150 | 169 | 0.025 | 50 |
| 160 | 203 | 0.030 | 50 |

[a]Feedstream (mol): 10% $H_2$, 10% $O_2$, 30% propylene, balance helium flow 150 cc/min; atmospheric pressure.

It is seen that a composition comprising gold and calcium on Ti-beta can catalyze the direct oxidation of propylene to propylene oxide. The conversion is 0.025 mole percent at 130° C. with a propylene oxide selectivity of 75 mole percent.

EXAMPLE 9
Catalyst Preparation and Epoxidation Process

Three catalysts (A, B, C) comprising gold on TS-1 (Si/Ti=30) were prepared in a manner similar to Example 5(b) by using the reagent amounts specified in Table 7.

TABLE 7

Quantities of Reagents for Catalyst Preparations

| Reagent | A (g) | B (g) | C (g) |
|---|---|---|---|
| $HAuCl_4.3H_2O$ | 0.1056 | 0.2089 | 0.4483 |
| TS-1(Si/Ti = 30) | 10.00 | 10.00 | 10.01 |
| $Mg(NO_3)_2.6H_2O$ | 2.00 | 2.00 | 2.00 |
| $Na_2CO_3$ | 0.18 | 0.38 | 0.56 |

Catalysts A, B, and C were evaluated in the direct oxidation of propylene as in Example 8 with the results shown in Table 8.

TABLE 8

Oxidation of Propylene (PP) to Propylene Oxide (PO) With Au/TS-1 Catalyst

| Catalyst | Conv PP (mol %) | Sel PO (mol %) |
|---|---|---|
| A[a] | 0.09 | 95.2 |
| B[a] | 0.15 | 92.9 |
| C[a] | 0.19 | 92.7 |
| C[b] | 0.87 | 92.0 |

[a]Catalyst, 5 cc; Feedstream (mol %): 10% $H_2$, 10% $O_2$, 30% propylene, balance helium; 110° C., atmospheric pressure, flow 250 cc/min.
[b]Catalyst (8 cc) calcined at 375° C. for 3 hr in air. Feedstream (mol %): 6.5% $H_2$, 6.5% $O_2$, 35% propylene, balance helium; 90° C., 185 psia (1276 kpa), flow 943 cc/min.

It is seen in Table 8 that at constant temperature, pressure and flow rate, as the gold loading is increased, the conversion of propylene also increases. It is also seen that as the pressure of the process is increased, the conversion of propylene is significantly increased. Selectivity remains about constant at greater than 90 mole percent under the process conditions shown.

EXAMPLES 10 (a–f)

Six catalysts were prepared as follows: Chloroauric acid (1.4526 g) was dissolved in water (500.0 cc). The total solution was divided into 10 portions of 50 cc each. A TS-1 support (Ti/Si=31) was prepared in a manner similar to that shown hereinabove for TS-1 having a Ti/Si of 27, with the exception that 1250.4 g of TEOS, 51.83 g of titanium tetra-n-butoxide, 1065.2 g of TPAOH, and 531.1 g deionized water were used. The TS-1 support obtained was crushed to greater than 60 mesh. The TS-1, in the amount shown in Table 9, was added to 50.0 cc of the gold solution, and the resulting suspension was stirred at room temperature for about 30 min. A promoter metal salt in the amount shown in Table 9 was added to each mixture, and the mixture was stirred for 1 hr.

TABLE 9

Catalyst Preparation

| Exp 10 | TS-1, g | Promoter (g) in addition to Na |
|---|---|---|
| a | 5.04 | none |
| b | 5.01 | $Mg(NO_3)_2.6H_2O$ (0.5050 g) |
| c | 5.00 | $Ca(NO_3)_2.4H_2O$ (0.4648 g) |
| d | 5.04 | $Ba(NO_3)_2$ (0.5128 g) |
| e | 5.03 | $Er(NO_3)_3.5H_2O$ (0.9023 g) |
| f | 5.03 | $Lu(NO_3)_3.x\ H_2O$ (0.9152 g) |

Sodium carbonate was added until the pH was 7.6 and the mixture was stirred for 1 hr. If necessary, more sodium carbonate was added to raise the pH to 7.6. The mixture was stirred overnight and then allowed to sit over the weekend at room temperature. The mixture was filtered. The filtered material was washed with water, then dried at 120° C. in air, then calcined in air over 8 hr to 400° C., and held at 400° C. for 5 hr. Each of the catalyst (5 cc) was tested in the oxidation of propylene with a flow of 150 cc/min of 30 percent propylene, 10 percent oxygen, 10 percent hydrogen, with the balance helium. Resuluts are set forth in Tables 10 and 11.

TABLE 10

PP Conversion/PO Selectivity (mole %)[a,b]

| T (° C.) | Hr on Stream | Ex. 10a (Na Only) | Ex. 10b (Mg) | Ex. 10c (Ca) | Ex. 10d (Ba) |
|---|---|---|---|---|---|
| 100 | 5.5 | 0.030/88.2 | 0.162/97.1 | 0.159/96.1 | 0.048/95.2 |
| 110 | 8.5 | 0.106/96.0 | 0.211/93.1 | 0.182/96.2 | 0.080/94.5 |
| 140 | 101.5 | 0.101/94.7 | 0.235/88.4 | 0.195/89.4 | 0.144/92.5 |
| 145 | 120.0 | 0.113/94.8 | 0.229/88.4 | 0.232/90.2 | 0.182/87.7 |
| 150 | 126.5 | 0.139/94.6 | 0.275/87.5 | 0.270/91.0 | 0.206/85.6 |
| 155 | 130.5 | 0.162/93.8 | 0.304/85.5 | 0.327/88.7 | 0.252/85.9 |

[a]PP = propylene; PO = propylene oxide
[b]Feed: 30% propylene, 10% oxygen, 10% hydrogen, balance helium; flow = 150 cc/min; pressure atmospheric

| T (° C.) | Hr on Stream | 10e (Er) | 10f (Lu) |
|---|---|---|---|
| 100 | 5.5 | 0.078/88.8 | 0.224/96.6 |
| 110 | 21.5 | 0.108/97.4 | 0.187/97.2 |
| 120 | 25.5 | 0.135/97.2 | 0.246/96.7 |
| 130 | 43.5 | 0.187/96.6 | 0.326/95.7 |
| 140 | 93.5 | 0.233/95.6 | 0.440/89.9 |
| 140[b] | 118.5 | 0.082/97.2 | 0.186/88.1 |
| 145 | 124.5 | 0.120/96.9 | 0.282/86.6 |
| 150 | 141.5 | 0.191/93.8 | 0.342/86.3 |
| 155 | 143.0 | 0.211/93.8 | 0.439/84.3 |

[a]PP = propylene; PO = propylene oxide
[b]Feed: 30% propylene, 10% oxygen, 10 % hydrogen, balance helium; Up to 140° C., flow rate was 150 cc/min; flow rate was raised at 140° C. to 500 cc/min; pressure atmospheric

TABLE 11

Water/Propylene Oxide Molar Ratio[a]

| T (° C.) | Hr on Stream | 10a (Na only) | Ex. 10b (Mg) | Ex. 10c (Ca) | Ex. 10d (Ba) |
|---|---|---|---|---|---|
| 100 | 5.5 | 23.05 | 7.17 | 8.38 | 12.39 |
| 110 | 8.5 | 3.93 | 5.70 | 7.90 | 14.92 |
| 140 | 101.5 | 7.35 | 7.33 | 9.86 | 9.34 |
| 145 | 120 | 7.24 | 7.63 | 9.50 | 11.21 |
| 150 | 126.5 | 7.40 | 8.23 | 10.87 | 12.44 |
| 155 | 130.5 | 6.61 | 9.09 | 10.84 | 12.30 |

[a] Feed: 30% propylene, 10% oxygen, 10% hydrogen, balance helium; flow rate = 150 cc/min; pressure atmospheric

| T (° C.) | Hr on Stream | Ex 10e (Er) | Ex 10f (Lu) |
|---|---|---|---|
| 100 | 5.5 | 8.16 | 5.97 |
| 110 | 21.5 | 5.88 | 5.92 |
| 120 | 25.5 | 5.87 | 6.60 |
| 130 | 43.5 | 6.99 | 8.74 |
| 140 | 93.5 | 7.54 | 13.73 |
| 140[b] | 118.5 | 8.82 | 33.12 |
| 145 | 124.5 | 7.64 | 13.5 |
| 150 | 141.5 | 7.35 | 16.55 |
| 155 | 143 | 7.81 | 13.68 |

[a]Feed: 30% propylene, 10% oxygen, 10% hydrogen, balance helium; Up to 140° C., flow rate was 150 cc/min. Flow rate was raised at 140° C. to 500 cc/min; pressure atmospheric It is seen in Tables 10 and 11 that catalysts containing gold and Group 2 or rare earth lanthanide matals supported on TS-1 are active catalysts for the direct oxidation of propylene to propylene oxide.

EXAMPLES 11 (a–d)

Four catalysts were prepared as follows: Chloroauric acid (1.4539 g) was dissolved in water (500.0 cc). A 50 cc portion of the gold solution was used to make each catalyst sample. A TS-1 support (Si/Ti=31; greater than 60 mesh) was added in the following amount to the solution: (a) 5.03 g; (b) 5.03 g; (c) 5.03 g; and (d) 5.05 g. The resulting suspension was stirred at room temperature for about 1 hr. The pH of the solution was adjusted to 7.6 with one of the following carbonate salts (a) lithium carbonate; (b) potassium carbonate; (c) rubidium carbonate; and (d) cesium carbonate. The mixture was stirred for 1 hr and then more carbonate salt was added if necessary to raise the pH to 7.6. The mixture was stirred overnight at room temperature. The mixture was filtered, and the filtered material was washed with water (150 cc). The wet solid was dried at 120° C. in air and then calcined in air over 8 hr to 400° C. and held at 400° C. for 5 hr. Each of the catalysts (5 cc) was tested in the oxidation of propylene with a flow of 150 cc/min of 30 percent propylene, 10 percent oxygen, 10 percent hydrogen, with the balance helium. Results are set forth in Tables 12 and 13.

TABLE 12

PP Conversion/PO Selectivity (mole %)[a,b]

| T (° C.) | Hr on Stream | Ex. 11a (Li) | Ex. 11b (K) | Ex. 11c (Rb) | Ex. 11d (Cs) | Ex. 13 (NH$_4$)[c] |
|---|---|---|---|---|---|---|
| 100 | 4.5 | .014/82.8 | .048/92.1 | .039/90.4 | .039/90.4 | .060/73.0 |
| 110 | 7.5 | .064/95.5 | .120/96.9 | .070/94.6 | .099/95.7 | .095/78.4 |
| 110 | 24 | .042/95.1 | .075/97.1 | .055/95.7 | .070/98.1 | .075/67.3 |
| 120 | 28 | .041/96.7 | .092/96.4 | .072/95.6 | .093/96.9 | .099/68.7 |
| 120 | 48.5 | .026/99.9 | .090/96.5 | .071/95.3 | .091/97.4 | .074/72.2 |
| 130 | 54 | .034/95.8 | .122/96.1 | .101/95.0 | .125/96.2 | .122/56.1 |
| 130 | 69 | .030/95.2 | .131/96.0 | .111/94.9 | .128/96.2 | .119/54.0 |
| 130 | 71.5 | — | — | — | — | .061/68.7 |
| 140 | 73 | .039/95.1 | .163/95.2 | .135/94.2 | .179/95.8 | .086/65.1 |
| 145 | 79 | .037/94.9 | .194/94.6 | .163/93.4 | .222/95.3 | .131/61.6 |
| 145 | 93.5 | .035/94.7 | .198/94.6 | .178/93.8 | .226/95.4 | .105/56.0 |
| 150 | 99.5 | .040/93.1 | .225/94.4 | .203/93.1 | .273/94.9 | .163/58.8 |
| 155 | 105 | .045/92.8 | .250/94.1 | .230/92.3 | .320/94.2 | |
| 160 | 117.5 | .050/92.3 | .290/93.6 | .270/89.0 | .366/93.7 | |
| 165 | 122.5 | .053/93.1 | .323/92.8 | .297/91.3 | .465/92.9 | |
| 170 | 143.5 | .061/93.0 | .364/90.0 | .331/88.3 | .479/91.8 | |
| 175 | 149 | .074/84.9 | .405/88.9 | .369/86.7 | .539/91.2 | |

[a]PP = propylene; PO = propylene oxide
[b]Feed: 30% propylene, 10% oxygen, 10% hydrogen, balance helium; flow rate = 150 cc/min; pressure atmospheric
[c]Flow rate increased in Ex. 13 at 71.5 hr to 500 cc/min.

TABLE 13

Water/Propylene Oxide Molar Ratio[a]

| T ° C. | Time hr | Ex. 11a (Li) | Ex. 11b (K) | Ex. 11c (Rb) | Ex. 11d (Cs) | Ex. 13 (NH$_4$)[b] |
|---|---|---|---|---|---|---|
| 100 | 4.5 | 50.38 | 12.71 | 8.92 | 10.72 | 38.29 |
| 110 | 7.5 | 8.90 | 5.49 | 7.43 | 5.90 | 28.78 |
| 110 | 24 | 8.62 | 3.47 | 7.35 | 4.45 | 40.95 |
| 120 | 28 | 10.28 | 6.05 | 5.80 | 5.42 | 48.57 |
| 120 | 48.5 | 13.21 | 6.97 | 8.11 | 5.98 | 60.97 |
| 130 | 54 | 14.52 | 6.60 | 7.60 | 5.32 | 94.93 |
| 130 | 69 | 15.2 | 7.33 | 6.64 | 5.31 | 98.42 |
| 130 | 71.5 | — | — | — | — | 40.80 |
| 140 | 73 | 11.54 | 6.67 | 6.64 | 5.23 | 47.74 |
| 145 | 79 | 13.64 | 6.95 | 6.74 | 5.58 | 56.81 |
| 145 | 93.5 | 12.33 | 7.40 | 7.52 | 6.09 | 64.88 |
| 150 | 99.5 | 16.59 | 8.16 | 6.73 | 5.68 | 64.00 |
| 155 | 105 | 16.80 | 8.04 | 7.79 | 5.84 | |
| 160 | 117.5 | 13.81 | 7.82 | 8.88 | 6.67 | |
| 165 | 122.5 | 11.97 | 9.51 | 7.79 | 6.46 | |
| 170 | 143.5 | 10.08 | 9.90 | 9.84 | 9.45 | |
| 175 | 149 | 11.87 | 11.43 | 11.24 | 10.56 | |

TABLE 13-continued

Water/Propylene Oxide Molar Ratio[a]

| T °C. | Time hr | Ex. 11a (Li) | Ex. 11b (K) | Ex. 11c (Rb) | Ex. 11d (Cs) | Ex. 13 (NH$_4$)[b] |
|---|---|---|---|---|---|---|

[a]Feed: 30% propylene, 10% oxygen, 10% hydrogen, balance helium; flow rate = 150 cc/min; pressure atmospheric
[a]How rate increased in Ex. 13 at 71.5 hr to 500 cc/min It is seen in Tables 12 and 13 that a catalyst comprising gold and a Group 1 promoter metal supported on a porous titanosilicate is an active catalyst for oxidizing propylene with oxygen to propylene oxide.

EXAMPLE 12

A catalyst was prepared as in Example 1 using the following amounts of reagents: chloroauric acid, 0.1225 g in water (50 cc); TS-1 support, 10.0157 g; magnesium nitrate, 1.99 g; and sodium carbonate, 0.1318 g. The catalyst (5 cc, 3.25 g) was tested in the oxidation of propylene with oxygen in the manner described in Example 2 with the results shown in Table 14.

TABLE 14

Oxidation of Propylene to Propylene Oxide[a,b]

| Time hr | T °C. | flow cc/min | % PP Conv | % PO Sel |
|---|---|---|---|---|
| 61 | 70 | 150 | 0.03 | 95.5 |
| 150 | 80 | 150 | 0.09 | 98.31 |
| 170 | 100 | 150 | 0.17 | 98.73 |
| 200 | 110 | 150 | 0.17 | 97.83 |
| 250 | 120 | 150 | 0.16 | 97.48 |
| 300 | 125 | 150 | 0.16 | 97.01 |
| 350 | 136 | 250 | 0.16 | 97.45 |
| 400 | 140 | 250 | 0.17 | 97.11 |
| 550 | 160 | 500 | 0.11 | 95.83 |
| 579 | 180 | 500 | 0.13 | 96.00 |
| 581[c] | 180 | 500 | 0.17 | 94.33 |

[a]PP = propylene; PO = propylene oxide
[b]Feed: 25% propylene, 10% oxygen, 10% hydrogen, balance helium; pressure atmospheric
[c]Feedstream also contained 1 mole percent water.

It is seen that the catalyst of Example 12 containing gold and magnesium on a TS-1 support is active and highly selective to propylene oxide at 580 hr on stream. The addition of water to the feedstream has a beneficial effect on raising the conversion.

EXAMPLE 13

A catalyst is prepared as in Example 11 with the exception that 5.05 g of TS-1 are used and ammonium carbonate is employed to adjust the pH. The catalyst is tested in the oxidation of propylene oxide is in Example 11 with the results shown in Tables 12 and 13. It is seen that propylene oxide is produced in a selectivity of over 50 mole percent.

What is claimed is:

1. A catalyst composition comprising gold on an amorphous titanosilicate.

2. The composition of claim 1 wherein the titanosilicate has pores ranging in size from 4 Å to about 200 Å in diameter.

3. The composition of claim 1 wherein the gold is present in an amount greater than 0.01 and less than 20 weight percent.

4. The composition of claim 1 wherein the catalyst is essentially free of the anatase phase of titanium dioxide.

5. The composition of claim 1 wherein the catalyst is substantially free of titanium dioxide.

6. The composition of claim 1 wherein the catalyst is essentially free of a Group VIII metal.

7. The composition of claim 1 wherein the composition is bound to or supported on a support.

8. The composition of claim 7 wherein the support is selected from silicas, aluminas, aluminosilicates, magnesia, titania, carbon and mixtures thereof.

9. The composition of claim 1 being prepared by a process comprising contacting the titanosilicate with a solution containing a gold compound selected from the group consisting of chloroauric acid, sodium chloroaurate, potassium chloroaurate, gold cyanide, potassium gold cyanide, and diethylamine auric acid trichloride, wherein the pH of the solution is between 5 and 11 and the pH is adjusted with a base selected from the group consisting of sodium hydroxide, sodium carbonate, potassium carbonate, cesium hydroxide, and cesium carbonate, the contacting being conducted at a temperature between 20° C. and 80° C.; and thereafter recovering solids and calcining the solids under air or under a reducing atmosphere or heating the solids in an inert atmosphere at a temperature between 250° C. and 800° C.

10. The composition of claim 9 wherein the gold compound is chloroauric acid.

11. The composition of claim 9 wherein the reducing atmosphere is hydrogen.

12. A catalyst composition comprising gold on an amorphous titanosilicate wherein the gold is present as particles having an average size of 10 Å or greater.

13. The catalyst composition of claim 12 wherein the gold is present as particles having an average size of greater than 10 Å and less than about 500 Å.

14. The catalyst composition of claim 12 wherein the titanosilicate has pores ranging in size from 4 Å to about 200 Å in diameter.

15. The catalyst composition of claim 12 wherein the gold is present in an amount greater than 0.01 and less than 20 weight percent.

16. The catalyst composition of claim 12 wherein the catalyst is essentially free of the anatase phase of titanium dioxide.

17. The catalyst composition of claim 12 wherein the catalyst is substantially free of titanium dioxide.

18. The catalyst composition of claim 12 wherein the catalyst is essentially free of a Group VIII metal.

19. The catalyst composition of claim 12 wherein the catalyst is bound to or supported on a support.

20. The catalyst composition of claim 19 wherein the support is selected from silicas, aluminas, aluminosilicates, magnesia, titania, carbon, and mixtures thereof.

21. The catalyst composition of claim 12 being prepared by a process comprising contacting the titanosilicate with a solution of a gold compound selected from the group consisting of chloroauric acid, sodium chloroaurate, potassium chloroaurate, gold cyanide, potassium gold cyanide, and diethylamine auric acid trichloride, wherein the pH of the solution is between 5 and 11 and the pH is adjusted with a base selected from the group consisting of sodium hydroxide, sodium carbonate, potassium carbonate, cesium hydroxide, and cesium carbonate, the contacting being conducted at a temperature between 20° C. and 80° C.; and thereafter recovering solids and calcining the solids under air or under a reducing atmosphere or heating the solids in an inert atmosphere at a temperature between 250° C. and 800° C.

22. The catalyst composition of claim 21 wherein the gold compound is chloroauric acid.

23. The catalyst composition of claim 21 wherein the reducing atmosphere is hydrogen.

* * * * *